United States Patent
Thompson et al.

(10) Patent No.: US 8,122,757 B2
(45) Date of Patent: Feb. 28, 2012

(54) PROPELLANT IGNITION TESTING APPARATUS HAVING A COMPRESSIVELY SEALABLE CHAMBER

(75) Inventors: Clay Thompson, Socorro, NM (US); Huseyin Koksal, Florence, NJ (US); Jesse Piotrowicz, Los Alamos, NM (US); Alex Myers, Cleveland, OK (US); Daniel Kitts, Socorro, NM (US); Joshua T. Fleming, Port Orchard, WA (US); David M. Baker, Bayfield, CO (US); Ian Montano, Rio Rancho, NM (US)

(73) Assignee: New Mexico Technical Research Foundation, Socorro, NM (US)

( * ) Notice: Subject to any disclaimer, the term of this patent is extended or adjusted under 35 U.S.C. 154(b) by 311 days.

(21) Appl. No.: 12/408,154

(22) Filed: Mar. 20, 2009

(65) Prior Publication Data
US 2010/0294023 A1    Nov. 25, 2010

(51) Int. Cl.
*G01N 33/22* (2006.01)
(52) U.S. Cl. .................................................. 73/35.17
(58) Field of Classification Search ................. 73/35.14, 73/35.17
See application file for complete search history.

(56) References Cited

U.S. PATENT DOCUMENTS

| | | | |
|---|---|---|---|
| 3,842,665 A | 10/1974 | Sober | |
| 4,068,591 A * | 1/1978 | Betts | 102/202.14 |
| 4,430,885 A | 2/1984 | Huskins et al. | |
| 4,759,215 A * | 7/1988 | Atchley et al. | 73/167 |
| 4,905,502 A | 3/1990 | Gram | |
| 5,052,817 A | 10/1991 | Bement et al. | |
| 5,652,381 A * | 7/1997 | Fuchs | 73/114.62 |
| 5,675,115 A * | 10/1997 | Hershkowitz et al. | 102/202 |
| 6,342,186 B1 | 1/2002 | Wingfield, III et al. | |
| 6,662,629 B2 | 12/2003 | Khadduri et al. | |
| 6,991,365 B1 * | 1/2006 | Pierorazio | 374/8 |

OTHER PUBLICATIONS

"The Closed Bomb Technique for Burning Rate Measurement At High Pressure" Arpad A. Juhasz and Channon F. Price.

* cited by examiner

*Primary Examiner* — Max Noori
(74) *Attorney, Agent, or Firm* — Robert W. Becker; Robert Becker & Associates

(57) ABSTRACT

A propellant ignition testing apparatus having a compressively sealable chamber. A fixed end plate assembly is fixedly mounted on a support structure. A test chamber assembly having a combustion chamber for accommodating propellant is provided, and an initiator ignites propellant accommodated in the combustion chamber. A moveable end plate is disposed adjacent to the test chamber assembly on a side thereof remote from the fixed end plate assembly. A device is mounted on the support structure for generating a compressive force, with the moveable end plate being operatively connected to a moveable component of the device for moving the moveable end plate toward the test chamber assembly for sandwiching the combustion chamber of the test chamber assembly in a compressively sealed manner between the fixed end plate assembly and the moveable end plate.

20 Claims, 6 Drawing Sheets

PROPELLANT IGNITION TESTING APPARATUS HAVING A COMPRESSIVELY SEALABLE CHAMBER

BACKGROUND OF THE INVENTION

The present application relates to a propellant ignition testing apparatus, also referred to as a closed bomb testing apparatus. In particular, the present application relates to a propellant ignition testing apparatus having a compressively sealable chamber.

A closed bomb or propellant ignition testing apparatus is used to measure the pressure that develops during combustion of a solid propellant after it is ignited within the combustion chamber of the apparatus. Such a chamber simulates the environment of, for example, a gun barrel. In the past, the propellant or combustion chamber was sealed by a threaded end cap, with a pressure relief system consisting only of a relief valve being provided.

It is an object of the present application to provide an improved propellant ignition testing apparatus that is more reliable and also safer.

BRIEF DESCRIPTION OF THE DRAWINGS

This object, and other objects and advantages of the present application, will appear more clearly from the following specification in conjunction with the accompanying schematic drawings, in which.

SUMMARY OF THE INVENTION

Figure 1:
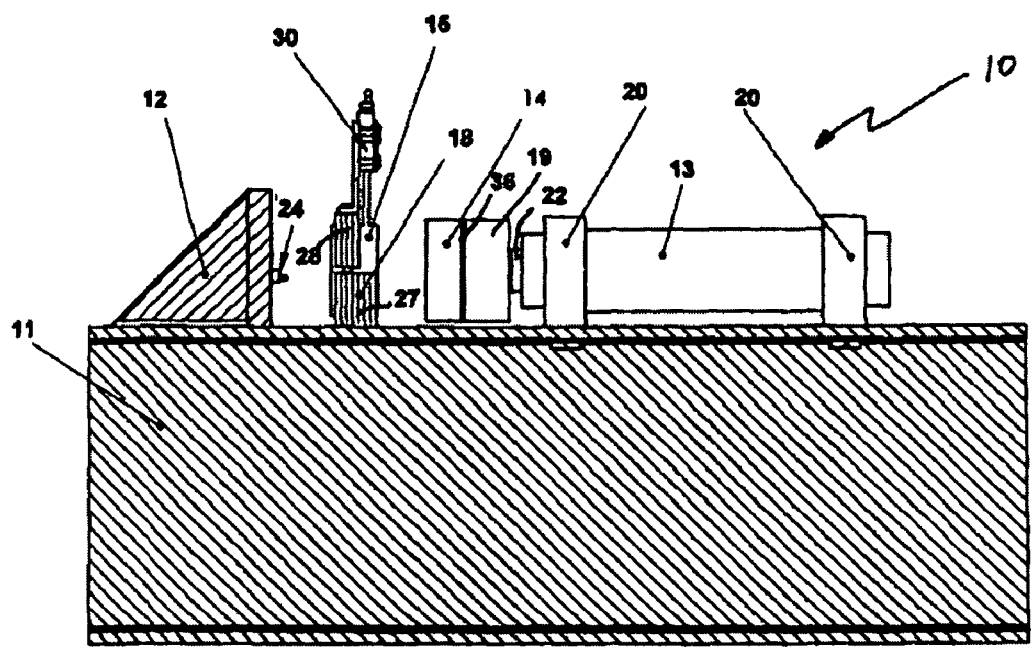
FIG. 1 is a partially cross-sectioned side view of one exemplary, single-beam mounted, embodiment of the propellant ignition testing apparatus of the present application, prior to sealing of the combustion chamber.

The propellant ignition testing apparatus of the present application comprises a support structure; a fixed end plate assembly that is fixedly mounted on the support structure; a test chamber assembly having a combustion chamber for accommodating propellant; means for initiating ignition of propellant accommodated in the combustion chamber of the test chamber assembly; a moveable end plate disposed adjacent to the test chamber assembly on a side thereof remote from the fixed end plate assembly; and a device mounted on the support structure for generating a compressive force, wherein the moveable end plate is operatively connected to a moveable component of the device for moving the moveable end plate toward the test chamber assembly such that the combustion chamber thereof is adapted to be sandwiched in a compressively sealed manner between the fixed end plate assembly and the moveable end plate.

The combustion chamber of the test chamber assembly is preferably connected to a pressure relief system. This pressure relief system comprises a rupture disk assembly to provide safe venting of gasses at a predetermined pressure, at which the rupture disk fails, to prevent overpressurization of the test chamber assembly. A remotely operated pressure relief valve can also be provided to allow for venting of the gasses, for example in the event that the pressure does not exceed the rupture disk capability. Once propellant is placed in the combustion chamber of the test chamber assembly, test personnel are able to relocate to a safe observation area, are able to then seal the chamber remotely, initiate the test, remotely vent the exhaust gasses, and open the chamber remotely, thus preventing any exposure to a pressurized test chamber assembly.

The propellant ignition testing apparatus of the present application is capable of handling and testing propellant of the order of magnitude of only a few grams, thus allowing for much smaller batches of propellant to be used than is possible with prior art devices, thus making research and development of new propellants more economical.

Further specific features of the present invention will be described in detail subsequently.

DESCRIPTION OF SPECIFIC EMBODIMENTS

Referring now to the drawings in detail, the propellant ignition testing apparatus of the present application is indicated, generally by the reference numeral 10. In the most basic configuration, the testing apparatus 10 comprises a support structure 11, a fixed end plate assembly 12, a device 13 for generating a compressive force, a moveable end plate 14, and a test chamber assembly 15 that is provided with a combustion chamber 16. The combustion chamber 16 is adapted to be sandwiched, in a compressively sealed manner, between the fixed end plate assembly 12 and the moveable end plate 14 by means of the device 13.

The fixed end plate assembly 12 is fixedly mounted to the support structure 11 in any convenient manner that will allow the fixed end plate to satisfactorily withstand the forces generated during the combustion of propellant that is disposed in the combustion chamber 16. By way of example only, the fixed end plate assembly 12 can be bolted to the support structure 11.

The test chamber assembly 15 is disposed adjacent to the fixed end plate assembly 12. In FIG. 1, the position of the test chamber assembly 15 relative to the fixed end plate assembly 12 is somewhat exaggerated. In particular, the test chamber assembly 15 could actually abut against the fixed end plate assembly 12. The test chamber assembly 15 itself is supported by a cradle assembly 18, which will be described in greater detail below.

The moveable end plate 14 is disposed on that side of the test chamber assembly 15 that is remote or opposite from the fixed end plate assembly 12. In particular, the moveable end plate 14 is operatively connected to the device 13 for generating compressive force, or at least is adapted to be acted upon by the device 13. In the illustrated embodiment, a coupler 19 is provided for connecting the moveable end plate 14 to the device 13. Finally, the device 13 for generating compressive force is mounted on the support structure 11 via the interposition of brackets 20.

Figure 2:
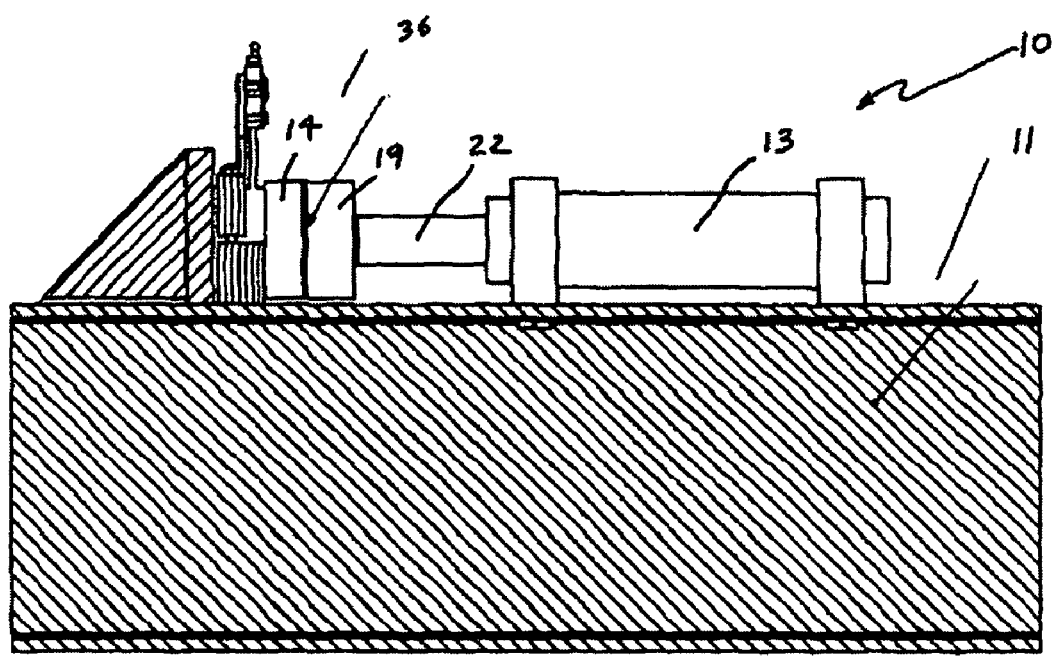
FIG. 2 is a partially cross-sectioned side view of the embodiment of FIG. 1 with the combustion chamber sealed.

In the illustrated embodiment, the device 13 for generating compressive force is illustrated as a piston/cylinder arrangement, wherein in FIG. 1 the piston 22 is shown in the retracted state so that in the open state of the testing apparatus 10 illustrated in FIG. 1, access is provided to the test chamber assembly 15 for loading propellant into the combustion chamber 16 thereof, as well as for easy inspection and maintenance of the test chamber assembly. FIG. 2 shows the sealed state of the combustion chamber 16 of the test chamber assembly 15, wherein the piston 22 in shown in the extended state, with the combustion chamber 16 being sandwiched in a compressively sealed manner between the fixed end plate assembly 12 and the moveable end plate 14.

In the embodiment described above, the device 13 for generating compressive force was described as a piston-cylinder arrangement. Such a piston/cylinder arrangement can be of any known type that provides enough holding force to maintain the compressive seal of the combustion chamber 16 of the test chamber assembly 15. For example, the piston/cylinder arrangement can be a hydraulic arrangement, a pneumatic arrangement, or a mechanically operating system. Other means for applying a compressive force could also be utilized, such as a worm gear system. A combination of the foregoing systems would also be conceivable. The device 13 is preferably remotely controlled.

The propellant ignition testing apparatus 10 of the present application also includes a means 24 for initiating ignition of propellant accommodated in the combustion chamber 16 of the test chamber assembly 15. In the embodiment of the testing apparatus illustrated in FIGS. 1 and 3, the initiating means or initiator 24 is a hot-wire initiator, and is shown disposed in the fixed end plate assembly 12. It should be noted that the initiator 24 could also be disposed in the test chamber assembly 15 itself. As can be seen from FIG. 3, an electrical feed-through 25 is provided for connection to the hot-wire initiator 24. The electrical feed-through 25 also leads to a remote control mechanism for activating the initiator 24.

Figure 3:
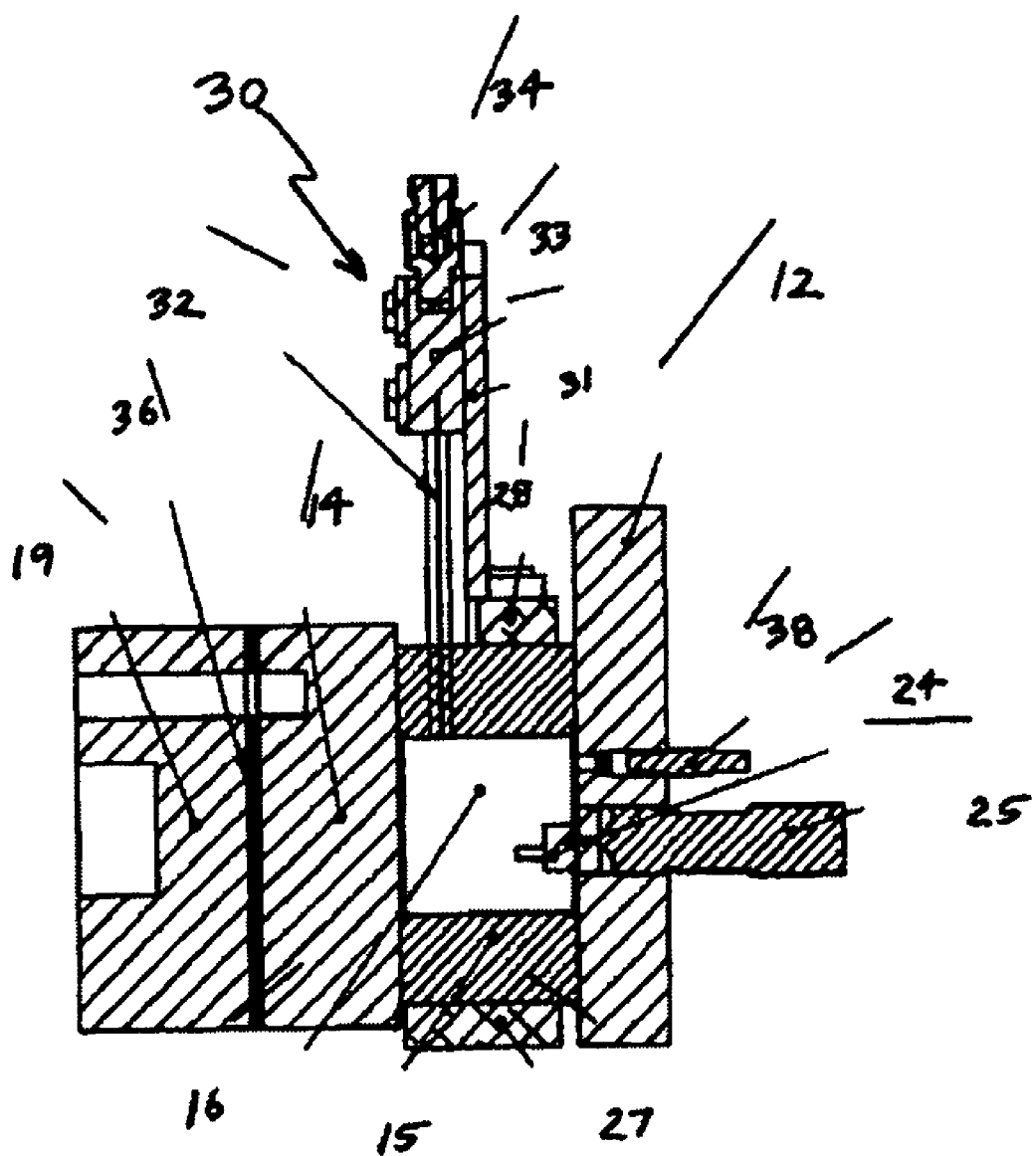
FIG. 3 is a cross-sectional side view showing the test chamber assembly of the testing apparatus of the present application.

As can be best seen in FIG. 3, the cradle assembly 18 comprises a bottom cradle 27 and a top cradle 28 for holding the test chamber assembly 15. A pressure relief system 30 is mounted on the top cradle 28 by means of a pressure relief system mounting bracket 31. The pressure relief system 30 itself comprises a pressure tube 32 that establishes communication between the combustion chamber 16 of the test chamber assembly 15 and a T-adapter 33, which connects to both a rupture disk safety head 34 and to another tube that leads to a remotely operated relief valve, which will be subsequently described in conjunction with FIG. 5. The rupture disk of the safety head 24 is configured to fail at a predetermined pressure to enable exhaust gasses to vent out of the safety head to prevent overpressurization of the combustion chamber. It is to be understood that the cradle assembly 18 for the test chamber assembly 15, and which also supports the pressure relief system 30, is not permanently attached to the support structure 11 to facilitate loading and inspection, as well as possible movement, of the test chamber assembly 15.

In the embodiment illustrated in FIGS. 1 to 3, a single I-beam is used as the support structure 11. The use of a single I-beam 11 as the main support structure allows for bending of the beam, resulting in a slight misalignment of the end plate 14 and of the test chamber assembly 15. Thus, pursuant to one embodiment of the present application, a malleable disk 36 is disposed between the moveable end plate 14 and the coupler 19, as well as optionally between the end plate 14 and the test chamber assembly 15, to compensate for bending in the support beam 11 and to insure a proper seal when the combustion chamber 16 is closed. Such a malleable disk could also be provided on the other side of the test chamber assembly 15 between it and the fixed end plate assembly 12.

The test chamber assembly 15 is preferably in the shape of a cylinder, since such a configuration is generally preferred for handling the compressive forces and internal pressures that are encountered during the combustion of propellant in the combustion chamber 16 of the test chamber assembly 15. However, other chamber configurations would also be conceivable, including square, rectangular and octagonal, where less pressure has to be accommodated.

As shown in FIG. 3, a pressure transducer 38 can also be provided to measure the pressure in the combustion chamber 16 of the test chamber assembly 15. Again, although the pressure transducer 38 is illustrated as being disposed in the fixed end plate assembly 12, it could also be provided in the test chamber assembly 15.

Depending upon the size of the components of the propellant ignition testing apparatus 10 of the present application, guide means could be provided for some of these components, such as for the test chamber assembly 15. For example, such guide means could be in the form of guide rails.

It should be noted that the moveable end plate 14 is mounted on the device 13 for generating compressive force, for example on the coupler 19 thereof, in a free-floating manner, thus allowing for lateral movement to insure a proper sealing of the combustion chamber 16 of the test chamber assembly 15.

Figure 4:
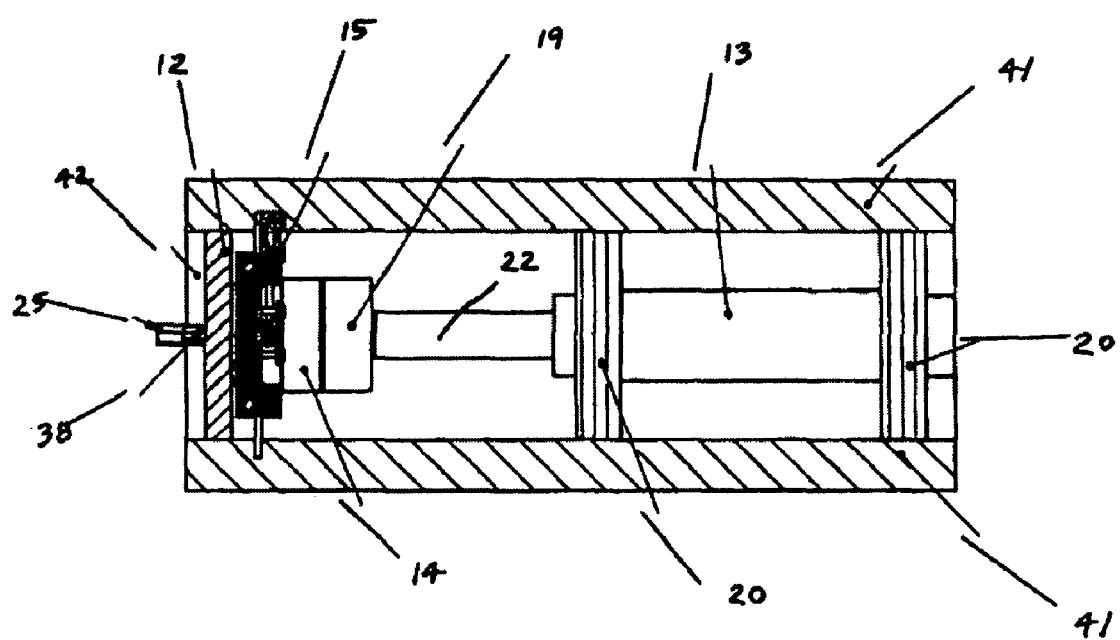
FIG. 4 is a top elevational view of a dual-beam mounted embodiment of the testing apparatus of the present application, with the combustion chamber sealed.

In the embodiment illustrated in FIGS. 1 to 3, a single I-beam was illustrated as the support structure 11. In FIG. 4, a preferred embodiment using two main support beams 41 is illustrated. The fixed end plate assembly 12 and the mounting brackets 20 for the device 13 are mounted to the support beams 41. A bottom plate 42 can be attached to maintain alignment of the test chamber assembly 15 during operation. The device 13 for generating compressive force, in this case again a piston/cylinder arrangement, is disposed in the mounting brackets 20. The coupler 19, such as a hydraulic coupler, is mounted to the piston 22 of the device 13.

In the dual-beam support configuration illustrated in FIG. 4, the malleable disk 36 shown in the embodiment of FIGS. 1-3 can be eliminated between the coupler 19 and the moveable end plate 14 in as much as there will be no bending moment. The test chamber assembly 15 is then sandwiched between the moveable end plate 14 and the fixed end plate assembly 12. Also illustrated are possible locations for the electrical feed-through 25 and the pressure transducer 38, although as indicated above, these components can be mounted in any convenient location that allows access to the inner combustion chamber 16 of the test chamber assembly 15.

Figure 5:
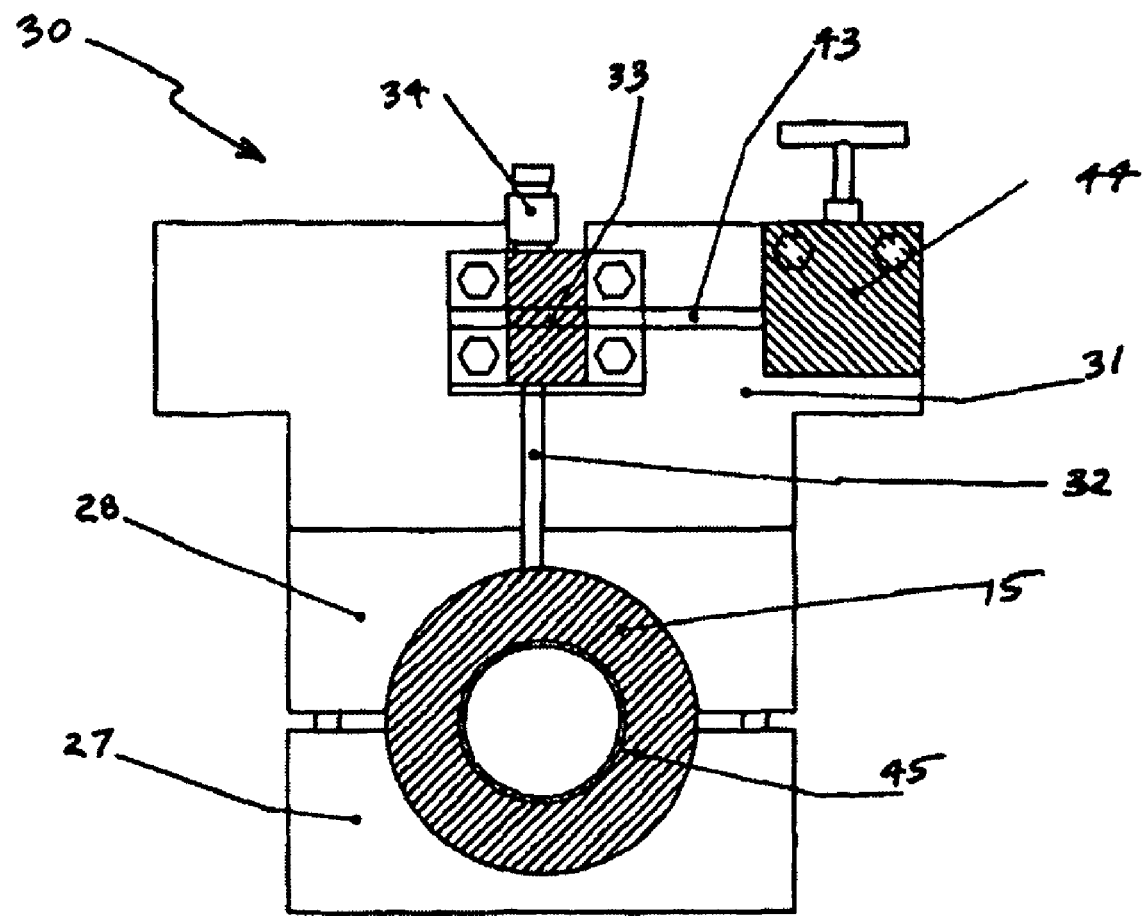
FIG. 5 is a partially cross-sectioned end view of one embodiment of a pressure relief system for the testing apparatus of the present application.

FIG. 5 illustrates a preferred embodiment of the test chamber assembly 15 and the pressure relief system 30. As described above, the cylindrical test chamber assembly 15 is mounted between the bottom cradle 27 and the upper or top cradle 28. The cradle assembly maintains the cylindrical chamber assembly at the correct vertical level when it is placed on the support structure 11, and allows for the mounting of the pressure relief system mounting bracket 31, to which the T-adapter 33 is mounted. Connected to the T-adapter are the pressure tube 32 as well as a further pressure tube 43, which communicate with the test chamber assembly 15 and a remotely operated relief valve 44 respectively. Also connected to the T-adapter 33 is the rupture disk safety head 34. To insure a proper seal, a gasket or O-ring 45 must be provided on both sides of the cylindrical test chamber assembly 15. In the embodiment illustrated in FIG. 5 both the remotely operated relief valve 44, and the remotely operated device 13 for generating compressive force can be utilized redundantly to vent gasses in the combustion chamber 16.

Figure 6:
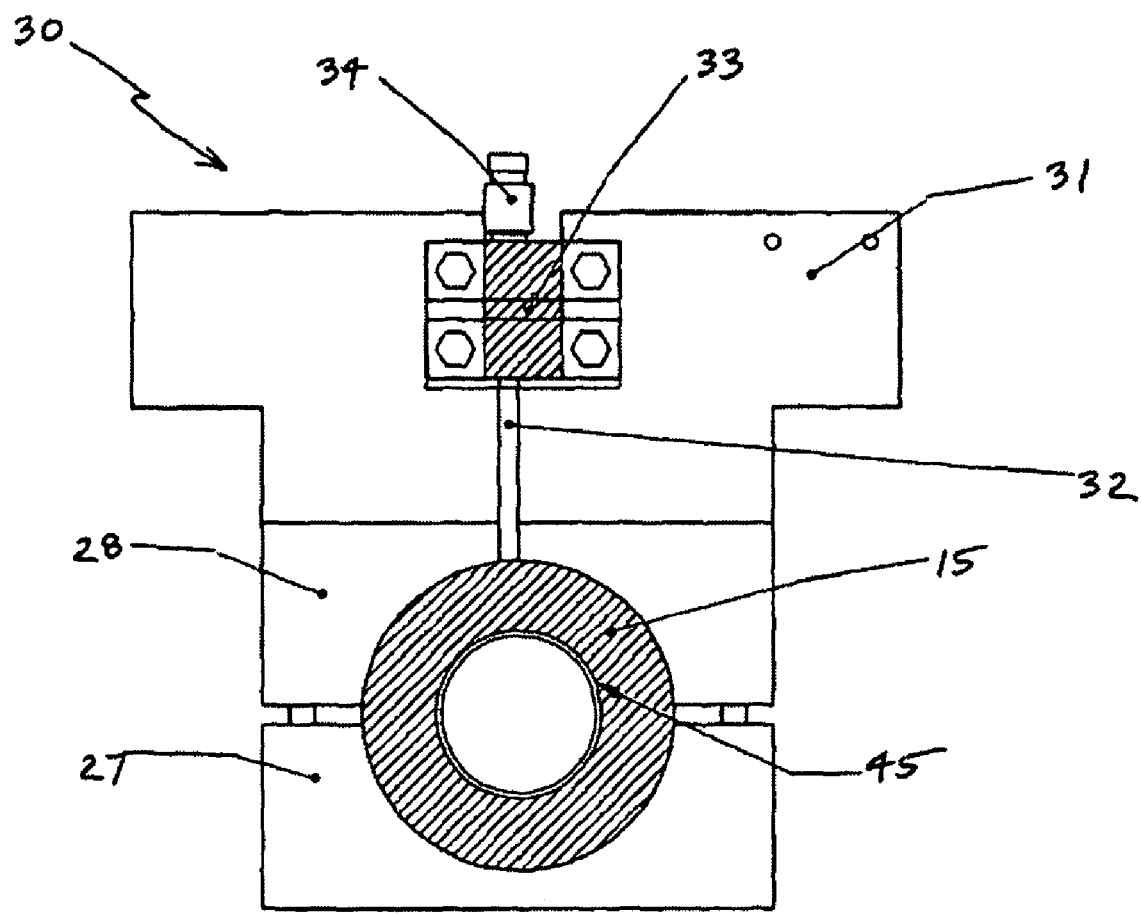
FIG. 6 is a partially cross-sectioned end view of an alternative embodiment of a pressure relief system for the testing apparatus of the present application.

FIG. 6 illustrates an alternative embodiment for the test chamber assembly 15 and for the pressure relief system 30. The cylindrical test chamber assembly 15 is again mounted between a bottom cradle 27 and an upper cradle 28, with the cradle assembly maintaining the test chamber assembly at the correct vertical level when it is placed upon the support structure, and allowing for the mounting of the pressure relief system mounting bracket 31, to which the adapter 33 is mounted. Connected to the adapter is the pressure tube 32 that communicates with the combustion chamber 16 of the test chamber assembly 15. Also connected to the adapter 33 is the rupture disk safety head 34. In this embodiment, the remotely operated device 13 for generating compressive force can be utilized to vent the pressure in place of a remotely operated relief valve as shown in the embodiment of FIG. 5. To insure a proper seal, again a gasket or O-ring 45 must be provided on both sides of the cylindrical test chamber assembly 15.

The present invention is, of course, in no way restricted to the specific disclosure of the specification and drawings, but also encompasses any modifications within the scope of the appended claims.

What we claim is:

1. A propellant ignition testing apparatus having a compressively sealable chamber, comprising:
   a support structure;
   a fixed end plate assembly fixedly mounted on said support structure;
   a test chamber assembly having a combustion chamber for accommodating propellant;
   means for initiating ignition of propellant accommodated in said combustion chamber of said test chamber assembly;
   a moveable end plate disposed adjacent to said test chamber assembly on a side of said test chamber assembly remote from said fixed end plate assembly;
   a device mounted on said support structure for generating a compressive force, wherein said moveable end plate is operatively connected to a moveable component of said device for moving of said moveable end plate toward said test chamber assembly such that said combustion chamber of said test chamber assembly is adapted to be sandwiched in a compressively sealed manner between said fixed end plate assembly and said moveable end plate; and
   a cradle assembly for said test chamber assembly.

2. A propellant ignition testing apparatus according to claim 1, wherein a pressure transducer is provided for measuring pressure in said combustion chamber of said test chamber assembly.

3. A propellant ignition testing apparatus according to claim 1, wherein a pressure relief system is operatively associated with said combustion chamber of said test chamber assembly and wherein said pressure relief system is mounted on said cradle assembly.

4. A propellant ignition testing apparatus according to claim 3, wherein said pressure relief system includes a pressure tube that communicates with said combustion chamber of said test chamber assembly and with a rupture disk safety head that is connected to said pressure tube.

5. A propellant ignition testing apparatus according to claim 4, wherein said pressure relief system further includes a pressure relief valve connected to said pressure tube.

6. A propellant ignition testing apparatus according to claim 5, further comprising means for remotely operating said pressure relief valve of said pressure relief system.

7. A propellant ignition testing apparatus according to claim 1, wherein said test chamber assembly has a cylindrical configuration.

8. A propellant ignition testing apparatus according to claim 1, wherein said means for initiating ignition is a hot-wire initiator disposed in said fixed end plate assembly.

9. A propellant ignition testing apparatus according to claim 1, wherein a coupler is disposed on said moveable component of said device for generating a compressive force, and wherein said moveable end plate is disposed on said coupler.

10. A propellant ignition testing apparatus according to claim 1, wherein said moveable end plate is adapted to be acted upon by said moveable component of said device for generating a compressive force.

11. A propellant ignition testing apparatus having a compressively sealable chamber, comprising:
    a support structure;
    a fixed end plate assembly fixedly mounted on said support structure;
    a test chamber assembly having a combustion chamber for accommodating propellant;
    means for initiating ignition of propellant accommodated in said combustion chamber of said test chamber assembly;
    a moveable end plate disposed adjacent to said test chamber assembly on a side of said test chamber assembly remote from said fixed end plate assembly;
    a device mounted on said support structure for generating a compressive force, wherein said moveable end plate is operatively connected to a moveable component of said device for moving of said moveable end plate toward said test chamber assembly such that said combustion chamber of said test chamber assembly is adapted to be sandwiched in a compressively sealed manner between said fixed end plate assembly and said moveable end plate:
    a coupler disposed on said moveable component of said device for generating a compressive force, wherein said moveable end plate is disposed on said coupler; and
    a malleable disk disposed between said moveable end plate and said coupler.

12. A propellant ignition testing apparatus having a compressively sealable chamber, comprising:
    a support structure;
    a fixed end plate assembly fixedly mounted on said support structure;
    a test chamber assembly having a combustion chamber for accommodating propellant;
    means for initiating ignition of propellant accommodated in said combustion chamber of said test chamber assembly;
    a moveable end plate disposed adjacent to said test chamber assembly on a side of said test chamber assembly remote from said fixed end plate assembly;
    a device mounted on said support structure for generating a compressive force, wherein said moveable end plate is operatively connected to a moveable component of said device for moving of said moveable end plate toward said test chamber assembly such that said combustion chamber of said test chamber assembly is adapted to be sandwiched in a compressively sealed manner between said fixed end plate assembly and said moveable end plate; and
    a malleable disk disposed between said moveable end plate and said test chamber assembly and between said fixed end plate assembly and said test chamber assembly.

13. A propellant ignition testing apparatus according to claim 1, wherein said device for generating a compressive force is a piston/cylinder arrangement, or a mechanical arrangement for generating a compressive force.

14. A propellant ignition testing apparatus according to claim 1, wherein said support structure is a single beam or a plurality of beams.

15. A propellant ignition testing apparatus according to claim 1, further comprising means for remotely operating said device for generating a compressive force.

16. A propellant ignition testing apparatus according to claim 11, wherein a cradle assembly is provided for said test chamber assembly.

17. A propellant ignition testing apparatus according to claim 12, wherein a cradle assembly is provided for said test chamber assembly.

18. A propellant ignition testing apparatus according to claim 12, wherein a coupler is disposed on said moveable component of said device for generating a compressive force, and wherein said moveable end plate is disposed on said coupler.

19. A propellant ignition testing apparatus according to claim 12, wherein said moveable end plate is adapted to be acted upon by said moveable component of said device for generating a compressive force.

20. A propellant ignition testing apparatus according to claim 12, wherein said device for generating a compressive force is a piston/cylinder arrangement, or a mechanical arrangement for generating a compressive force.

* * * * *